United States Patent [19]
Yang

[11] Patent Number: 5,442,030
[45] Date of Patent: Aug. 15, 1995

[54] POLYIMIDES CONTAINING FLUORINATED AROMATIC DIAMINE UNITS

[75] Inventor: Zhenyu Yang, Wilmington, Del.

[73] Assignee: E. I. Du Pont de Nemours and Company, Wilmington, Del.

[21] Appl. No.: 136,528

[22] Filed: Oct. 14, 1993

[51] Int. Cl.$^6$ ............................................. C08G 73/10
[52] U.S. Cl. ................................. 528/353; 528/125; 528/128; 528/172; 528/173; 528/174; 528/176; 528/183; 528/220; 528/229; 528/350; 526/242
[58] Field of Search ............... 528/183, 176, 174, 172, 528/173, 125, 128, 220, 229, 350, 353; 526/242

[56] References Cited

U.S. PATENT DOCUMENTS

| | | | |
|---|---|---|---|
| 5,037,917 | 8/1991 | Babb et al. | 526/242 |
| 5,091,500 | 2/1992 | Lysenko et al. | 528/183 |
| 5,159,038 | 10/1992 | Babb et al. | 526/242 |
| 5,225,515 | 7/1993 | Lysenko et al. | 528/125 |

*Primary Examiner*—Morton Foelak
*Assistant Examiner*—P. Hampton-Hightower

[57] ABSTRACT

Polyimides are made from the novel diamines 1,2-bis(3-aminophenyl)perfluorocyclobutane, 1,2-bis(3- or 4-aminophenyl)perfluorocyclobutene, -cyclopentene and -cyclohexene, by reaction with aromatic carboxylic anhydrides. The polyimides are useful for coatings and films.

9 Claims, No Drawings

POLYIMIDES CONTAINING FLUORINATED AROMATIC DIAMINE UNITS

FIELD OF THE INVENTION

This invention provides novel polyimides, which are made with novel diamines containing aminophenyl groups which are bound to fluorinated carbocyclic rings. The polyimides are useful as coatings and films.

TECHNICAL BACKGROUND

Polyimides are useful polymers, often having very good high temperature and electrical properties. Such polymers are often used as films, particularly in electrical and electronic applications as insulators and dielectrics.

U.S. Pat. No. 5,091,500 describes polybenzoxazoles which contain perfluorocyclobutane rings. No mention is made of polyimides.

SUMMARY OF THE INVENTION

This invention concerns a polyimide comprising the repeat unit

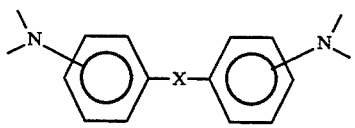

wherein X is selected from the group consisting of

and

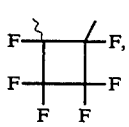

n is an integer selected from the group consisting of 2, 3, and 4; and provided that:
when X is (I) each nitrogen atom is attached to the 4 position of the respective benzene ring, or each nitrogen atom is attached to the 3 position of the respective benzene ring;
when X is (II) the nitrogen atom is attached to the 3 position of the respective benzene ring; and each nitrogen atom is part of an aromatic imide group.

It is preferred in structures (III) and (IV) that when X is

n is 2.

This invention also concerns a compound of the formula

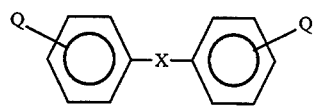

wherein X is selected from the group consisting of

and

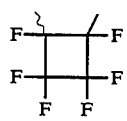

n is 2, 3, or 4;
both of Q are either —NH₂ or —NO₂; and provided that:
when both of Q are —NO₂, X is (II), and each of Q is attached to the 3 position of the respective benzene ring or each of Q is attached to the 4 position of a respective benzene ring;
when both of Q are —NH₂, and X is (I), each of Q is attached to the 4 position of the respective benzene ring or each of Q is attached to the 3 position of the respective benzene ring; and
when both of Q are —NH₂, and X is (II), each of Q is attached to the 3 position of the respective benzene ring.

DETAILS OF THE INVENTION

The dinitro compounds disclosed herein are useful as intermediates for the production of diamines. The dinitro compounds disclosed and claimed herein are 1,2-bis(3-nitrophenyl)perfluorocyclobutane and 1,2-bis(4-nitrophenyl)perfluorocyclobutane. The preparation of these dinitro compounds is described in Examples 1, 2 and 7.

The diamines disclosed herein are useful as monomers in the preparation of polyimides. The diamines disclosed herein are 1,2-bis(3-aminophenyl)perfluorocyclobutane, 1,2-bis(4-aminophenyl)perfluorocyclobutene, 1,2-bis(4-aminophenyl)perfluorocyclopentene, and 1,2-bis(4-aminophenyl)perfluorocyclohexene. The first two of these diamines are prepared by the reduction of precursor dinitro compounds, as described in Examples 3 and 8. During the reduction of the dinitro compound to a diamine, wherein the nitro groups are in the 4 position of each benzene ring, the cyclobutane ring is defluorinated to a cyclobutene ring.

The diamines containing the perfluorocyclobutene, -pentene, and -hexene groups can be made by "protecting" the amino group of 3- or 4-bromoaniline by reaction with 1,2-bis(chlorodimethylsilyl)ethane and with 2.1 equivalents of n-butyllithium to give the protected amine [see S. Djuric et al., Tetrahedron Letters, vol. 22, p. 1787 (1981)]. The protected amine is then reacted with n-butyllithium to give the corresponding lithium compound. The lithium compound is reacted with perfluorocyclobutene, perfluorocyclopentene or perfluorocyclohexene, and then the amino group is deprotected in 1N KOH to give the desired diamines [see M. Hanzawa et al., J. Chem. Soc. Chem. Com., p. 206 (1992) and S. Iwata et al., J. Org. Chem., vol. 57, p. 3726 (1992)].

The above diamines are useful in the preparation of polyimides, specifically polyimides containing the repeat unit

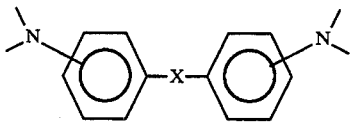

with the provisos listed above. The benzene rings are numbered as shown below:

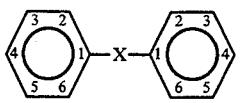

This repeat unit is part of an imide group, in this case an aromatic imide group.

By an "aromatic imide group" is meant that in the imide group,

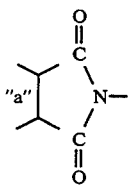

the bond marked "a" will be part of an aromatic ring. Since imides are most commonly made from cyclic anhydrides, at least some of the imide groups in the instant polyimides are derived from cyclic aromatic carboxylic anhydrides. Useful cyclic aromatic carboxylic anhydrides include pyromellitic dianhydride, benzophenone dianhydride, biphenyl dianhydride, oxydiphthalic anhydride, hexafluoroisopropylidenediphthalic anhydride, or an arylenedioxydiphthalic anhydride. Preferred repeat units have the formula

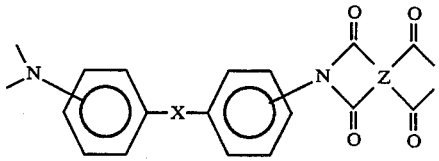

wherein Z is selected from the group consisting of

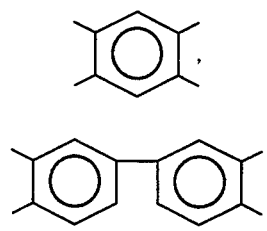

and

-continued

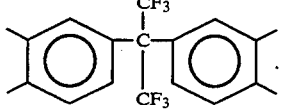

The repeat units disclosed herein comprise either all or some of the repeat units in the claimed polyimides. Thus, polyimide repeat units derived from other diamines (and/or more than one type of anhydride) may also be present, as may other types of linkages, such as ester linkages, so a poly(imide-ester) is formed. Thus, the claimed polymers may be homopolymers or copolymers.

The polyimides herein can be made by known methods and such methods are illustrated in the Examples. The polyimides are useful as coatings or films. These films are particularly useful as insulators and dielectrics in electrical and electronic applications.

EXAMPLE 1

Synthesis of Para-nitrotrifluorostyene

To a stirred mixture of acid-washed Zn (15 g) and tetraglyme was added iodotrifluoroethylene (25.7 g) at room temperature. After the addition was complete, the resulting mixture was stirred at room temperature for four hours. Excess Zn was removed by filtration under nitrogen, followed by addition of tetrakis(triphenylphosphine)palladium (1.2 g) and para-nitroiodobenzene (26.1 g) . The reaction mixture was heated at 65° C. overnight, and then poured into hexane (200 mL) and triturated. The hexane was decanted, and the trituration was repeated twice with hexane. The combined hexane layers were washed with water and dried over $MgSO_4$. After removal of hexane, the residue was purified by chromatography on silica gel using hexane as eluent to give desired product (17.1 g). $^{19}F$ NMR ($CDCl_3$): −94.5 (dd, J=56.7 Hz, J=33.3 Hz, 1F), −109.4 (dd, J=108.2 Hz, J=56.6 Hz, 1F), −177.8 (dd, J=108.8 Hz, J=33.3 Hz, 1F). $^1H$ NMR ($CDCl_3$): 7.65 (d, J=9.0 Hz, 2H), 8.30 (d, J=8.8 Hz, 2H). IR(nujol): 1752 (s), 1600 (s), 1529 (s), 1462 (s), 1350 (s), 1301 (s), 1158 (s).cm$^{-1}$ Anal: Calcd for $C_8H_4F_3NO_2$: C, 47.29; H, 1.97; F,28.08; N, 6.90. Found: C, 46.63; H, 2.04; F, 27.55; N, 6.51.

EXAMPLE 2

Dimerization of Para-nitrotrifluorostyene

Para-nitrotifluorostyene (12.0 g) was heated at 147° C. under nitrogen for 27.5 hours and then purified by chromatography on silica gel (hexane:ethyl acetate=90:5 to 90:10) to give the desired product (10.6 g) as cis and trans isomers. $^{19}F$ NMR: one isomer: −122.1 (dm, J=229.2 Hz, 2F), −127.6 (dm, J=229.0 Hz, 2F), −167.1 (m, 2F); another isomer: −124.3 (dm, J=223.3 Hz, 2F), −126.0 (dm, J=223.0 Hz, 2F), −168.5 (m, 2F). $^1H$ NMR: one isomer: 8.35 (d, J=8.7 Hz, 4H), 7.75 (d, J=8.8 Hz, 4H); other isomer: 8.25 (d, J=8.8 Hz, 4H), 7.48 (d, J=8.8 Hz, 4H). IR(neat): 3090 (w), 1609 (s), 1526 (s), 1351 (s), 258 (s), 1197 (s) . Anal: Calcd for $C_{16}H_8F_6N_2O_4$: C, 47.29; H, 1.97; N, 6.90. Found: C, 46.93; H, 2.10; N, 6.37.

EXAMPLE 3

Synthesis of
1,2-Bis(4-aminophenyl)tetrafluorocyclobutene

To a stirred solution of 1,2-bis(4-nitrophenyl)hexafluorocyclobutane (15.0 g), $SnCl_2 \cdot 2H_2O$ (83.0 g) and ethanol (300 mL) was slowly added a mixture of $NaBH_4$(1.5 g) in ethanol (30 mL) at room temperature (exothermic reaction). After the addition was complete, the resulting mixture was stirred at room temperature overnight and then poured into ether (500 mL) and water (500 mL). A solution of NaOH was added until the solids disappeared. The ether layer was separated and aqueous layer was extracted with ether ($2 \times 200$ mL). The combined ether layers were washed with water, and dried over $MgSO_4$. After removal of $MgSO_4$, the ether layer was treated with HCl gas. The solids (13.4 g, 95%) were obtained after filtration.

Above solids (8.5 g) was treated with 20% aqueous NaOH solution in 300 mL of ether at 0° C., the ether layer was separated and aqueous layer was extracted with ether. The combined ether layers were washed with water, and dried over $MgSO_4$. After evaporation of the ether, red solids (5.5 g) were obtained. By TGA, decomposition temperature was a round 130° C. under air when heated at 20° C./min. $^{19}F$ NMR ($CDCl_3$): $-114.0$ (s). $^1H$ NMR($CDCl_3$): 7.50 (d, J=8.6 Hz, 4H), 6.60 (d, J=8.5 Hz, 4H), 3.96 (br, 4H). UV (ethanol): $\eta_{max}$363 nm ($\epsilon$=27465), 301 nm ($\epsilon$=14013) nm and 239 nm ($\epsilon$=14013), c=0.0550 g/l ethanol. Anal: Calcd for $C_{16}H_{12}F_4N_2$: C, 62.34; H, 3.90; F, 24.68; N, 9.09. Found: C, 63.20; H, 3.87; F, 24.01; N, 9.05.

EXAMPLE 4

Preparation of Polyimide from Diamine and Pyromellitic Dianhydride (PMDA)

To a 25 mL three necked flask fitted with a mechanical stirrer and a condenser topped with an $N_2$ inlet was charged with the diamine of Example 3 (1.0 g) and 8 g of N-methyl pyrrolidone (NMP). The mixture was stirred until a clear solution was obtained and PMDA (0.71 g) was added in one portion and the resulting mixture was stirred at room temperature overnight. The polyamic acid solution was spread on a glass plate at 50° C. and some solvent was slowly evaporated at 80° C. for 1.5 hours. The film was cured by heating at 80° C. for 40 minutes; 100° C. for 30 minutes, warmed up to 280° C. at a rate of 10° C./min. and at 280° C. for 30 minutes. This heat treatment converted the polyamic acid to polyimide. The IR absorption peaks of the polyimide appeared at 1740 and 1980 $cm^{-1}$.

The polymer had a glass transition temperature temperature at 242.2° C. By TGA, the polymer showed 10% weight loss temperatures of about 545° C. under nitrogen and 520° C. under air, respectively, when heated at 20° C./min.

EXAMPLE 5

Preparation of Polyimide from Diamine and 3,4,3'4'-Diphenyltetracarboxlic Dianhydride To a 50 mL three necked flask fitted with a mechanical stirrer and a condenser topped with an $N_2$ inlet was charged with the diamine of Example 3 (1.54 g) and 14 mL of N-methyl pyrrolidone (NMP). The mixture was stirred until a clear solution was obtained and the flask was cooled in an ice-acetone bath. Then 3,4,3'4'-diphenyltetracarboxylic dianhydride (1.47 g) was added in one portion and the resulting mixture was stirred at this temperature to room temperature for 3 hours, then at room temperature overnight. The polyamic acid solution was spread on a glass plate at 50° C. and some solvent was slowly evaporated at 80° C. for 1.5 hours. The film was cured by heating at 80° C. for 40 minutes; 100° C. for 30 minutes, warmed up to 280° C. at a rate of 10° C./min. and at 280° C. for 30 minutes. This heat treatment converted the polyamic acid to polyimide. The IR absorption peaks of the polyimide appeared at 1715 and 1980 $cm^{-1}$. This film had a tensile strength 11.6 kpsi, modulus 299.6 kpsi and 5.3% elongation.

The polymer had a glass transition temperature temperature at 311.4° C. By TGA, the polymer showed 10% weight loss at temperatures of about 565° C. under air when heated at 20° C./min.

EXAMPLE 6

Preparation Of Polyimide from Diamine and 2,2'-Bis(3,4-dicarboxyphenyl) hexafluoro-propane Dianhydride (6FDA)

To a 50 mL three necked flask fitted with a mechanical stirrer, a condenser topped with an $N_2$ inlet was charged with the diamine of Example 3 (1.00 g) and 9 mL of N-methyl pyrrolidone (NMP). The mixture was stirred until a clear solution was obtained and the flask was cooled in an ice-acetone bath. The 6FDA (1.44 g) was added in one portion and the resulting mixture was stirred at this temperature to room temperature for 0.5 hour then at room temperature 4 hours. The polyamic acid solution was spread on a glass plate at 50° C. and solvent was slowly evaporated at 80° C. for 1.5 hours. The film was cured by heating at 80° C. for 40 minutes; 100° C. for 30 minutes, warmed up to 280° C. at a rate of 10° C./min. and at 280° C. for 30 minutes. This heat treatment converted the polyamic acid to polyimide. The IR absorption peaks of the polyimide appeared at 1720 and 1785 $cm^{-1}$ and the peak of carboxylic acid disappeared. This film had a tensile strength 15.18 kpsi, modulus 323.6 kpsi and 8.4% elongation.

The polymer had a glass transition temperature temperature of 308° C. By TGA, the polymer showed 10% weight loss temperatures of about 540° C. under air when heated at 20° C./min.

EXAMPLE 7

Preparation of
1,2-Bis(3-nitrophenyl)hexafluorocyclobutane

To a stirred mixture of Zn (22.0 g) and 200 mL of tetraglyme was slowly added trifluorovinyl iodide (42.0 g) at room temperature and the resulting mixture was stirred at room temperature overnight. $^{19}F$ NMR analysis of the reaction mixture indicated that the reaction was complete. After excess Zn was removed by filtration under nitrogen, meta-nitroiodobenzene (44.0 g) and $Pd(PPh_3)_4$ (1.3 g) were added and the resultant reaction mixture was stirred at 70° C. overnight. TLC indicated no meta-nitroiodobenzene. After being heated to 140° to 145° C. for 150 hours the reaction mixture was triturated 3 times with a mixture of hexane and ethyl acetate (4:1). The combined organic layers were washed with water, dried over $MgSO_4$. After removal of solvents, residue (35.3 g) was recrystalized from hexane and ethyl acetate to give 19.8 g of pure desired product. Mother liquid was concentrated to give a viscous liquid, which was purified by chromatography on silica gel (hexane/ethyl acetate=95/5 to 85/15) to give 9.9 g of the desired product. Total yield was 29.7 g. $^{19}$F NMR indicated that the product was a mixture of two isomers and major isomer: −124.5 (d, J=222.6 Hz, 2F), −126.2 (d, J=222 Hz, 2F), −168.6 (s, 2F); minor isomer: −122.4 (d, J=228.1 Hz, 2F), −127.8 (d, J=228.2 Hz, 2F), −167.4 (s, 2F). $^1$H NMR: major isomer: 8.43–8.40 (m, 4H), 7.90 (d, J=7.80 Hz, 2F), 7.74 (t, J=7.9 Hz, 2H); minor isomer: 8.25 (dm, J=7.4 Hz, 2H), 8.12 (s, 2H), 7.55 (m, 4H). Anal: Calcd for $C_{16}H_8F_6N_2O_4$: C, 47.31; H, 1.98; F, 28.06; N, 6.90. Found: C, 47.30; H, 2.06; F, 26.91; N, 6.39.

EXAMPLE 8

Preparation of 1,2-Bis(3-aminophenyl)hexafluorocyclobutane

To a stirred solution of $SnCl_2.2H_2O$ (83.0 g) and 1,2-bis(meta-nitrophenyl)hexafluorocyclobutane (15.0 g) in 300 mL of ethanol was added $NaBH_4$ (1.5 g) at room temperature over 20 minutes. After the addition was complete, the reaction mixture was stirred at room temperature for 3 hours and at 60° C. for one hour, and then poured into a mixture water and ether (500 mL/500 mL) and treated with NaOH solution. The ether layer was separated and aqueous layer was extracted with ether (2×300 mL). The combined ether layers were washed with NaOH solution and dried over $MgSO_4$. After removal of the solvent, residue (13.8 g) was purified by bulb-to-bulb distillation (ca. 170° C./0.05 mmHg) twice to give 12.0 g of viscous product. $^{19}$F NMR: major isomer: −125.0 (dm J=222 Hz, 2F), −125.9 (dm, J=dm, J 222 Hz, 2F), −160.3 (s, 2F). minor isomer: −122.1 (dd, J=225.1 Hz, J=3.4 Hz, 2F), −128.7 (dd, J=255.1 Hz, J=2.4 Hz, 2F), −165.0 (s, 2F); $^1$H NMR: major isomer: 7.22 (t, J=7.8 Hz, 2H), 6.96 (d, J=7.8 Hz, 2H), 6.86 (s, 2H), 6.77 (dm, J=8.1 Hz, 2H), 3.76 (s, 4H); minor isomer: 7.04 (t, J=7.1 Hz, 2H), 6.63 (d, J=6.6 Hz, 2H), 6.58 (m, 4H), 3.66 (s, 4H). Anal: Calcd for $C_{16}H_{12}F_6N_2$: C, 55.50; H, 3.49; F, 32.92; N, 8.09. Found: C, 55.47; H, 3.71; F, 31.12; N, 7.90.

EXAMPLE 9

Preparation of Polyimide from 1,2-Bis(3-aminophenyl)hexafluorocyclobutane and 3,4,3'4'-Diphenyltetracarboxlic Dianhydride To a 50 mL three necked flask fitted with a mechanical stirrer and a condenser topped with an $N_2$ inlet was charged with the diamine of Example 8 (1.38 g) and 8 g of N-methyl pyrrolidone (NMP). The mixture was stirred until a clear solution was obtained and 3,4,3'4'-diphenyltetracarboxlic dianhydride (1.173 g) was added in one portion and the resulting mixture was stirred at room temperature for one hour. After an additional 5 g of NMP was added, the mixture was stirred at room temperature for 20 hours. Some solution was slowly poured into water in a blender and a white powder was precipitated, which was washed with water and dried at 110° C. under vacuum for 6 hours. $^1$H NMR (DMAC-d$_9$): 12.24 (br, COOH), 8.27–6.88 (m, ArH). The polyamic acid solution was spread on a glass plate at 80° C. under air and then heated to 280° C. using following schedule: 80° C. for 40 minutes; 100° C. for 30 minutes, warmed up to 280° C. at a rate of 10° C./min. and at 280° C. for 30 minutes. This heat treatment converted the polyamic acid to polyimide. The IR absorption peaks of the polyimide appeared at 1715 and 1980 cm$^{-1}$. The film was strong but somewhat brittle.

The polyimide had a glass transition temperature at 351° C. By TGA, the polymer shows 10% weight loss temperatures of about 530° C. under air and 545° C. under nitrogen, respectively, when heated at 20° C./min.

EXAMPLE 10

Preparation of Polyimide from 1,2-Bis(3-aminophenyl) hexafluorocyclobutane and 2,2'-Bis(3,4dicarboxyphenyl) hexafluoropropane Dianhydride (6FDA)

To a 50 mL three necked flask fitted with a mechanical stirrer and a condenser topped with an $N_2$ inlet was charged with the diamine of Example 8 (1.20 g) and 11.5 g of N-methyl pyrrolidone (NMP). The mixture was stirred until a clear solution was obtained and 6FDA (1.54 g) was added in one portion and the resulting mixture was stirred at room temperature for 20 hours. Some polyamic acid solution was slowly poured into water in a blender and a white powder was precipitated, which was washed with water and dried at 110° C. under vacuum for 20 hours. $^1$H NMR (DMAC-d$_9$): 12.25 (br, COOH), 8.27–6.88 (m, ArH). The polyamic acid solution was spread on a glass plate at 80° C. under air and then heated to 280° C. using following schedule: 80° C. for 40 minutes; 100° C. for 30 minutes, warmed up to 280° C. at a rate of 10° C./min. and at 280° C. for 30 minutes. This heat treatment converted the polyamic acid to polyimide. The IR absorption peaks of the polyimide appeared at 1725 and 1985 cm$^{-1}$ and the peak of carboxylic acid (3440 cm$^{-1}$) disappeared. The film was strong but somewhat brittle.

The polymer had a glass transition temperature temperature at 314° C. By TGA, the polymer has a 10% weight loss temperature of about 545° C. under nitrogen when heated at 20° C./min.

What is claimed is:

1. A polyimide comprising the repeat unit

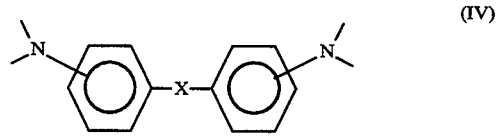

(IV)

wherein each nitrogen atom is part of an aromatic imide group and X is selected from the group consisting of

(I)

and

(II)

n is an integer selected from the group consisting of 2, 3, and 4; and provided that:

when X is (I) each nitrogen atom is attached to the 4 position of the respective benzene ring, or each nitrogen atom is attached to the 3 position of the respective benzene ring;

when X is (II) the nitrogen atom is attached to the 3 position of the respective benzene ring.

2. A polyimide according to claim 1 wherein the aromatic imide group is derived from cyclic aromatic carboxylic anhydrides selected from the group consisting of pyromellitic dianhydride, benzophenone dianhydride, biphenyl dianhydride, oxydiphthalic anhydride, biphenyl dianhydride, oxydiphthalic anhydride, hexafluoroisopropylidoene-diphthalic anhydride, and arylenedioxy-diphthalic anhydride.

3. A polyimide according to claim 1 wherein the repeat units have the formula

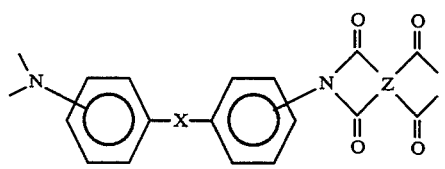

ps wherein Z is selected from the group consisting of

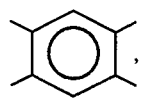

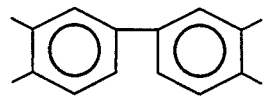

and

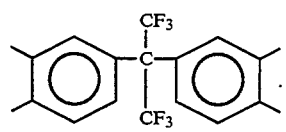

4. A polyimide as recited in claim 1 which is a homopolymer.

5. A polyimide as recited in claim 1 which is a copolymer.

6. A polyimide as recited in claim 3 which is a homopolymer.

7. A polyimide as recited in claim 3 which is a copolymer.

8. A polyimide as recited in claim 1 wherein X is (I) and n is 2.

9. A polyimide as recited in claim 1 wherein X is (II).

* * * * *